United States Patent [19]
Jonkman et al.

[11] Patent Number: 5,976,114
[45] Date of Patent: Nov. 2, 1999

[54] AORTIC CANNULA WITH REDUCED VELOCITY FLOW-THROUGH TIP

[75] Inventors: Kenneth R. Jonkman, Grand Rapids; Paul F. Rom, Kentwood, both of Mich.

[73] Assignee: Medtronic, Inc., Minneapolis, Minn.

[21] Appl. No.: 09/070,884

[22] Filed: Apr. 30, 1998

[51] Int. Cl.[6] ............................. A61M 5/00; A61M 5/32
[52] U.S. Cl. ..................... 604/264; 604/272; 604/30
[58] Field of Search .................... 604/264, 272, 604/30, 31, 273–275, 508, 513, 39, 523, 537, 93, 46, 280

[56] References Cited

U.S. PATENT DOCUMENTS

| | | | |
|---|---|---|---|
| 1,845,343 | 2/1932 | Salerni | 604/264 |
| 2,147,334 | 9/1939 | Moss | 604/264 |
| 3,828,767 | 8/1974 | Spiroff | 604/264 |
| 4,863,441 | 9/1989 | Lindsay et al. | 604/280 |
| 5,084,033 | 1/1992 | O'Neill et al. | |
| 5,171,218 | 12/1992 | Fonger et al. | |
| 5,300,022 | 4/1994 | Klapper et al. | 604/35 |
| 5,330,433 | 7/1994 | Fonger et al. | |
| 5,354,288 | 10/1994 | Cosgrove et al. | |
| 5,616,137 | 4/1997 | Lindsay | |
| 5,643,226 | 7/1997 | Cosgrove et al. | |
| 5,662,619 | 9/1997 | Zarate | 604/272 |
| 5,685,865 | 11/1997 | Cosgrove et al. | |
| 5,725,495 | 3/1998 | Strukel et al. | 604/44 |
| 5,846,219 | 12/1998 | Vancaillie | 604/35 |
| 5,848,996 | 12/1998 | Eldor | 604/272 |
| 5,876,383 | 3/1999 | Grooters et al. | 604/264 |

OTHER PUBLICATIONS

Groom RC, Hill AG, Kuban B, Oneill W, Akl BF, Speir AM, Koningsberg J, Sprissler GT, Shakoor M, Massimiano S, Burton NA, Albus RA, Macmanus Q and Lefrak EA, "Aortic Cannula Velocimetry" *Perfusion* 1995; 10: 183–188.

"3M™ Sarns™ Soft–flow Aortic Cannula" ©3M 1994.

*Primary Examiner*—Ronald K. Stright, Jr.
*Assistant Examiner*—Sharon Finkel
*Attorney, Agent, or Firm*—Foley & Lardner

[57] ABSTRACT

An improved aortic cannula is formed from a cannula body and a tip provided on the distal end of the cannula body wherein the tip is designed to accommodate the fluid flow requirements of an extracorporeal bypass system while simultaneously minimizing any possible adverse impact of the cannula and fluid flow on the vessel in which the cannula is received. The tip has an axial fluid discharge aperture provided at the distal end thereof through which a portion of the fluid exiting the cannula flows. In addition, at least one lateral fluid discharge aperture is provided in the sidewall of the tip. A scoop or other diverting member is formed in the sidewall to direct a portion of the fluid flowing through the tip to exit the cannula through the lateral fluid discharge apertures.

28 Claims, 2 Drawing Sheets

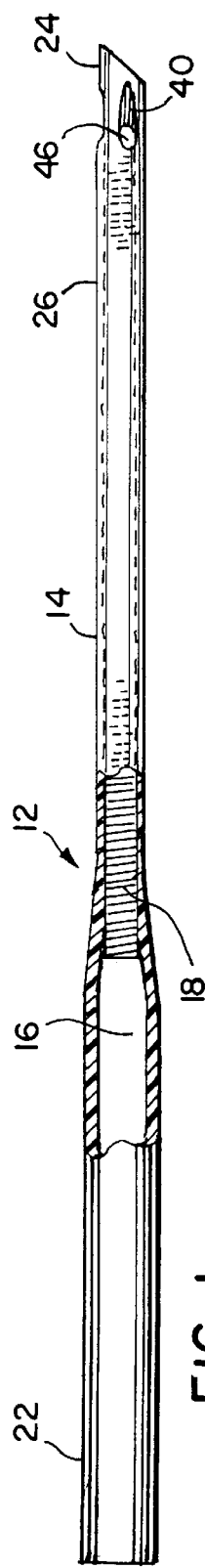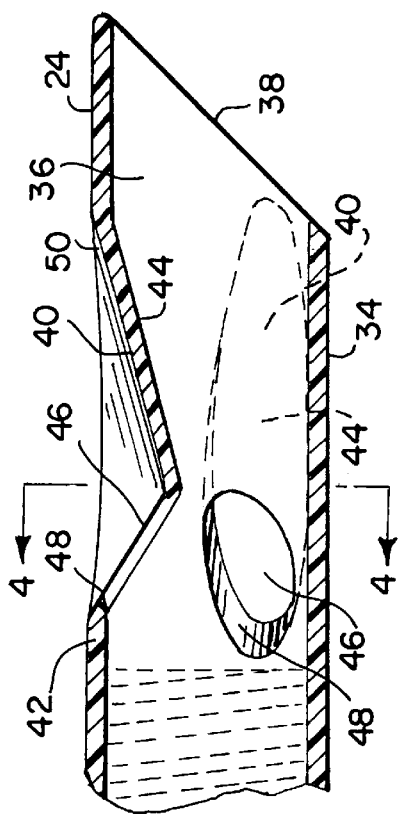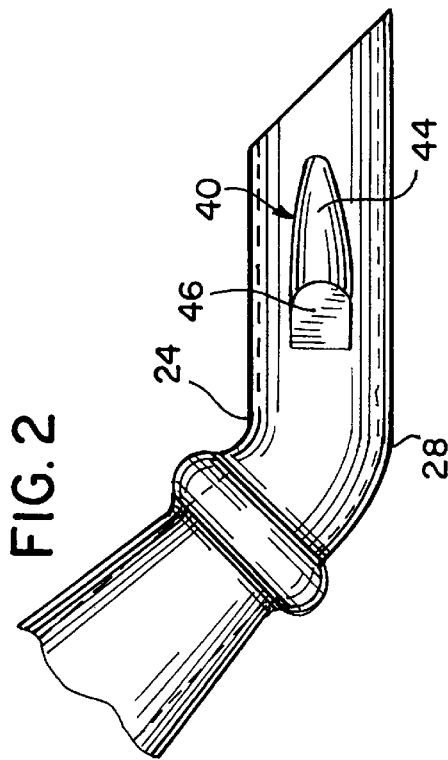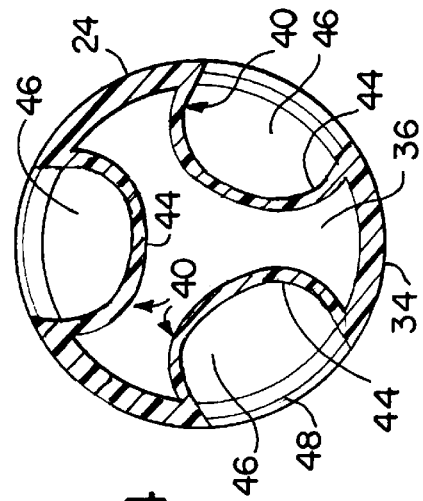
FIG. 1
FIG. 3
FIG. 4
FIG. 2

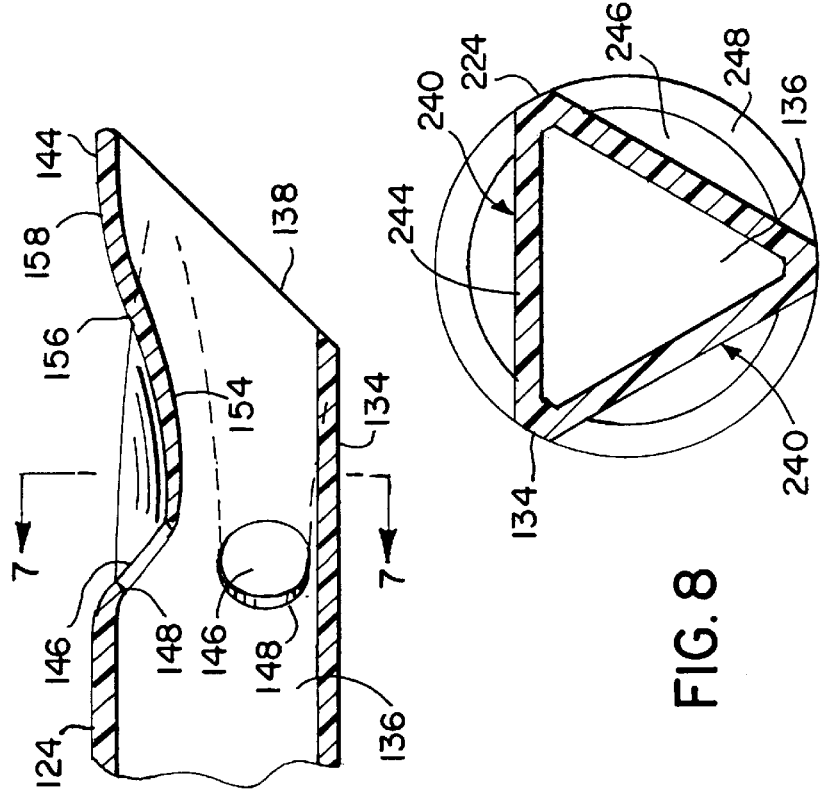
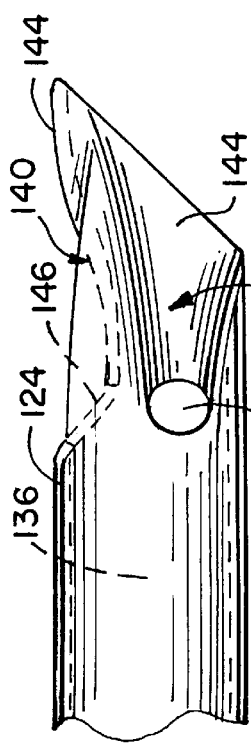
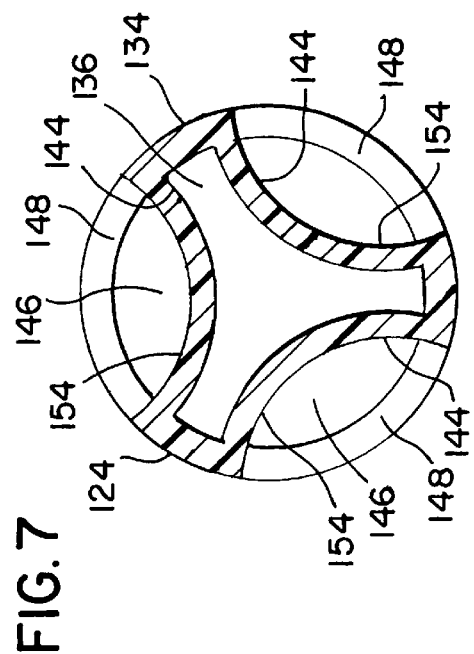
FIG. 5
FIG. 6
FIG. 7
FIG. 8

AORTIC CANNULA WITH REDUCED VELOCITY FLOW-THROUGH TIP

FIELD OF THE INVENTION

This invention relates to an aortic cannula incorporated as a component of the extracorporeal bypass circuit utilized during heart surgery and, more particularly, to the structure of the flow-through tip of the cannula and a method of making the aortic cannula.

BACKGROUND OF THE INVENTION

During traditional operations involving the blood circulatory system such as open-heart surgery, a patent's blood is typically removed from the body, oxygenated, and then returned to the body under pressure. Typically, blood is returned from this extracorporeal circuit to the patient's aorta through an aortic cannula. The aorta is a vessel which experiences high internal fluid pressures during a normal heart operation, therefore it is desired to minimize any trauma suffered by the aorta during these operations such as incisions. The challenge is to design an aortic cannula with the smallest diameter tip to minimize the necessary incision in the aorta, but will accommodate the necessary fluid flow rates without damaging the patient's blood or aorta.

Another factor which challenges the designers of aortic cannulas is avoiding concentrated, high velocity fluid flow from the tip of the cannula into the aorta commonly known as a "jet blast" effect. Many patients having this type of surgery already have atheromatous material and/or adherent thromba within the aorta. Directing a blast or jet of blood against the wall of the aorta could easily dislodge small pieces of these materials from the aorta causing strokes or blood clots.

The challenge at hand is to design an aortic cannula, and specifically the distal tip of the cannula to accommodate the necessary volume of fluid flow while simultaneously minimizing the impact on the aorta as a result of the diameter of the tip and the avoidance of any jet blast effect on the interior wall of the aorta. Other cannula designs are seen in U.S. Pat. Nos. 5,616,137 to Lindsay, 5,643,226 to Cosgrove, et al., 5,084,033 to O'Neill, et al., and 5,330,433 to Fonger, et al.

SUMMARY OF THE INVENTION

The aortic cannula according to the invention overcomes the problems of the prior art by accommodating the fluid flow demands while minimizing the detrimental impact of the cannula and the fluid flow therethrough on the patient's aorta.

In a first aspect, the invention is directed to an improved aortic cannula formed from a cannula body and a fluid discharge tip provided at the distal end of the cannula body. The tip has at least one axial fluid discharge aperture provided at the distal end thereof. Preferably, this aperture is substantially aligned with the axis of the lumen of the tip. Preferably, the axis of the center point of the axial fluid discharge aperture is both parallel to and aligned directly with the longitudinal axis of the lumen. In addition to this aperture, at least one lateral fluid discharge aperture is provided in the sidewall of the tip, proximally of the axial fluid discharge aperture. A diverting member or scoop is formed in the sidewall of the tip immediately adjacent to the lateral fluid discharge aperture. The diverting member extends radially inwardly into the lumen of the tip and is contoured to redirect a portion of the fluid flowing through the tip through the lateral fluid discharge aperture.

In the preferred embodiment, the cross-sectional area of the lumen proximally of the lateral fluid discharge aperture is substantially the same as the cross-sectional area of the lumen distally of the lateral fluid discharge aperture. With this structure, the aggregate velocity of the fluid exiting the tip is minimized because a portion of the fluid passing through the tip is removed through the lateral fluid discharge apertures while the fluid remaining in the tip encounters substantially the same cross-sectional area as before removal of a portion of the fluid. Therefore, the fluid exiting the distal fluid aperture has been slowed dramatically.

In the preferred embodiment, three lateral fluid discharge apertures are incorporated into three fluid diverting members or scoops provided in the sidewall of the tip. The three scoops are preferably positioned at the same point along the longitudinal length of the tip and are preferably equally spaced around the perimeter of the tip.

The particular design of the scoop can have several different configurations. In one embodiment, the scoop projects radially inwardly into the lumen and is substantially linear in cross section parallel to the longitudinal axis of the lumen of the tip and is arcuate in cross section transverse to the longitudinal axis of the lumen. In another embodiment, the scoop is substantially linear in cross section both parallel and transverse to the longitudinal axis of the lumen. In still another embodiment, the scoop is contoured such that it is arcuate in cross section both parallel and transverse to the longitudinal axis of the tip. A complex arcuate shape formed of concave and convex surfaces can be utilized to create desired flow patterns of the fluid emanating from the tip.

In another aspect, the invention is directed to a method of making an aortic cannula having a tip with substantially the same structure as described above.

BRIEF DESCRIPTION OF THE DRAWINGS

FIG. 1 is a side elevational view of an aortic cannula according to the invention;

FIG. 2 is a side elevational of an alternative embodiment of the distal tip of the aortic cannula according to the invention;

FIG. 3 is a cross-sectional view of the distal tip of FIG. 1;

FIG. 4 is a cross-sectional view of the distal tip taken along lines 4—4 of FIG. 3;

FIG. 5 is a side elevational view of a second embodiment of the distal tip according to the invention;

FIG. 6 is a cross-sectional view of the distal tip of the aortic cannula of FIG. 5;

FIG. 7 is a cross-sectional view of the distal tip of the aortic cannula taken along lines 7—7 of FIG. 6; and FIG. 8 is a cross-sectional view of a third embodiment of the distal tip of the aortic cannula similar to the view seen in FIG. 4, showing the flat planar scoops of this embodiment.

DESCRIPTION OF THE PREFERRED EMBODIMENT

Referring now to the drawings and to FIG. 1 in particular, an aortic cannula 12 according to the invention is shown. The cannula 12 comprises a cannula body 14 having a lumen 16 extending therethrough and, preferably, a wire reinforcement 18 extending along at least a portion of the length of the cannula body 14. The proximal end 22 of the cannula body 14 has an increased diameter so that the cannula 12 can be fluidly connected to a conventional bypass circuit. A reduced velocity tip 24 is provided on the distal end 26 of the cannula body 14. In the preferred embodiment, the reduced velocity tip is axially aligned with the cannula body 14; however, an alternative embodiment seen in FIG. 2 incorporates a bend 28 to redirect the flow laterally from the axis of the cannula body 14. Preferably the reduced velocity tip 24 is integrally molded with the cannula body 14.

In practice, the proximal end 22 of the cannula 12 is connected to the terminal end of a cannula emanating from the bypass pump (not shown) of the extracorporeal circuit. The reduced velocity tip 24 of the cannula is adapted to be inserted into an incision formed in a patient's aorta. Blood flows from the bypass pump through the aortic cannula 12 back into the patient's aorta under sufficient pressure to achieve distribution throughout the vasculature system.

Turning now to FIGS. 1, 3 and 4, the first embodiment of the reduced velocity tip will be described in greater detail. The tip 24 comprises a body portion 34 having a lumen 36 formed therein with a fluid aperture aligned with the axis of the body portion. This aperture, namely a distal flow aperture 38, is provided at the terminal end of the tip 24. In addition, at least one additional fluid aperture, namely a diverting port or lateral fluid discharge aperture 46, is formed in the sidewall of the body portion 34, proximally of the distal flow aperture. The lateral fluid discharge aperture 46 is preferably formed in the sidewall of a fluid diverting member or scoop 40 provided in the sidewall of the tip 24. The preferred embodiment of the reduced velocity tip 24 incorporates three fluid diverting scoops 40 and corresponding lateral fluid discharge apertures 46. However, it is to be understood that it is within the scope of this invention to incorporate a single fluid diverting scoop and aperture or a plurality of said scoops and apertures. The necessary fluid flow characteristics for the aortic cannula 12 will determine the number of scoops and apertures necessary. The fluid flow characteristics will also help determine the contour of the scoops. As expressly shown below are arcuate and planar scoops. It will be understood that a wide variety of scoop configurations are within the scope of the invention. For example, the scoops could be U-shaped in transverse cross section wherein the corners of the U-shape are rounded. Alternatively, the corners of the U-shape could be well defined so that the sidewalls and bight portion are substantially planar.

Incorporation of both lateral and axial fluid apertures, 46 and 38 respectively, into a single tip 24 creates an effective structure for accommodating the fluid flow requirements of the aortic cannula while simultaneously minimizing any traumatic shear effect on the blood flowing therethrough while simultaneously minimizing any jet blasting effect on the sidewall of the aorta. All of this is accomplished by reducing the velocity of fluid flow and breaking up the fluid flow emanating from the tip 24.

It is well known that average velocity is a function of the fluid flow rate divided by the effective area through which the fluid flows. In this embodiment of the reduced velocity tip 24, a portion of the fluid passing through the main lumen 16 of the cannula 12 exits the cannula 12 through the lateral fluid discharge apertures 46 while the balance of the blood flowing therethrough exits the cannula through the distal flow aperture 38. The cross-sectional area of the tip 24 proximally of the fluid diverting scoops 40 is the same as the cross-sectional area of the tip immediately adjacent to the distal flow aperture 38. Therefore, the effective area encountered by the blood flowing through the tip is the same proximally of the scoops 40 as it is distally of the scoops 40. However, a portion of the blood flowing through the tip 24 is discharged from the tip 24 through the fluid diverting ports 46. Therefore, a reduced volume of blood encounters the same cross-sectional area within the tip distally of the scoops 40. This reduced volume of fluid within the same cross-sectional area results in a reduced fluid flow velocity. In addition, the scoops and corresponding aperture serve to break up the fluid flow exiting the tip thereby reducing the jet blast effect. In the preferred embodiment, the cross-sectional area of both the distal end of the tip and the distal flow aperture are substantially equal to the cross-sectional area of the tip proximally of the lateral fluid discharge apertures 46. However, the cross-sectional area of these distal components can also be greater than the proximal end of the tip lumen.

The blood which exits the reduced velocity tip 24 through the fluid diverting scoops 40 flows along the exterior surface of the tip and eventually encounters the slower moving blood exiting the distal flow aperture 38. The combination of the essentially stagnant blood immediately surrounding the body portion 34 of the reduced velocity tip 24 along with the slow moving blood emanating from the distal flow aperture 38 combines to dramatically slow the velocity of the blood entering the aorta through the lateral fluid discharge apertures 46. The jet blast effect is reduced through the combination of the multiple apertures for discharging the blood from the aorta cannula along with the increase in effective area experienced by the blood as it flows through the axial fluid aperture of the tip. A tip according to the invention accommodates the fluid flow requirements of a typical bypass system while diverting and slowing the flow of fluid therethrough to avoid damage to the blood or the vessel in which the blood is being introduced.

The particular structure of the first embodiment of the reduced velocity tip 24 is seen in FIGS. 1, 3 and 4. In this embodiment, three flow diverting scoops 40 are formed in the sidewall 42 of the body portion 34 of the tip 24. The scoops 40 extend radially inwardly but not to such an extent that they entirely obstruct the flow of the fluid to the distal flow aperture 38. Only a portion of the fluid flowing through the lumen encounters the scoops.

In the preferred embodiment, each scoop comprises an arcuate sidewall 44 and the previously described lateral fluid discharge aperture 46, the aperture 46 being defined by the aperture edge 48. Preferably, the aperture edge 48 is circular wherein the axis of the center point of the circle extends radially outwardly from the axis of the body portion 34 at an angle of approximately fifteen degrees, co-linear with the axis of the arc of the scoop. However, as seen in FIG. 2, the edge 48 can have more complex shapes such as the depicted "D-shaped" aperture.

The axial cross section of the body portion 34 of the tip 24 shows that the sidewall 44 of the scoop is substantially linear from the aperture edge 48 to the sidewall 42 of the body portion 34. However, the transverse cross section seen in FIG. 4 shows that the sidewall 44 is arcuate in the transverse direction. The depth of the arc tapers from its deepest point immediately adjacent to the aperture edge 48 to its narrowest point immediately adjacent to the terminal end 50 of the scoop 40. Preferably, the transition or blending of the scoop into the sidewall of tip 24 is gradual.

In the preferred embodiment, each of the three fluid diverting scoops 40 are equally spaced radially around the perimeter of the body portion 34 of the tip 24. In addition, each of the scoops 40 are provided at the same position along the length of the body portion 34 of the tip 22. It is understood that the angular orientation and position of the scoops 40 can be altered to accommodate and create different flow characteristics from the cannula 12. For example, the scoops can be staggered along the length of the tip. Alternatively, the angular orientation of the scoops with respect to one another can be altered to increase or decrease the flow from one particular side of the tip relative to another.

A second embodiment of the scoop design is seen in FIGS. 5 and 6. Reference numerals for elements of the second embodiment which are similar to the elements of the first embodiment will be increased by one hundred over the description of the first embodiment.

In the second embodiment, the reduced velocity tip 124 similarly includes at least one, and preferably three lateral fluid discharge apertures 146 incorporated into three fluid diverting scoops 140 and at least one axial fluid discharge aperture, namely the distal flow aperture 138. Once again, the scoops 140 are positioned proximately of the distal flow aperture 138 and extend radially inwardly a short distance into the lumen 136 of the body portion 134. The primary difference between the first and second embodiments lies in the structure and contour of the scoop wall 144. In the second embodiment, the wall 144 is contoured for the purpose of controlling the fluid flow characteristics of the blood which passes over the surface thereof. When viewing an axial cross section of the scoop as seen in FIG. 6, it is seen that a first portion 154 of the scoop wall 144 is arcuate, specifically concave with respect to the wall 142 of the body portion 134. The radius of the first portion 154 is extends radially outwardly from the axis of the body portion 134 and the radius of the first portion 154 does not pass through the axis of the body portion 134. In the preferred embodiment, the radiased first portion extends from the aperture edge 148 to a point which is approximately the midpoint of the length of the scoop wall 144. At this approximate midpoint 156, the concave first portion 154 of the scoop wall transitions into a second portion 158 of the scoop wall 144. In the preferred embodiment, the second portion 158 is convex relative to the cross section of the wall 142 of the body portion 134. The radius of the arcuate, convex second portion 158 of the scoop wall extends in the opposite direction from the radius of the arcuate first portion 154 of the scoop wall 144. Preferably, the arcuate or convex second portion of the scoop wall extends from the midpoint 156 to the terminal edge 150 of the scoop 140.

In the second embodiment of the tip, it is believed that the complex arcuate shape of the scoop wall 144 creates a more efficient and less turbulent flow pattern for the blood exiting the cannula 12, although emperical testing has not been conducted to confirm this theory. The concave structure of the first portion 154 of the scoop wall gently redirects the flow of a portion of the blood passing through the tip 124 radially outwardly. The transition from the concave to the convex second portion 158 of the scoop wall 144 assists in redirecting the flow in the axial direction of the lumen 136 of the body portion 134. The gentle radius of these two portions is beneficial to prevent undue shear and trauma to the blood.

A third embodiment of the structure of the reduced velocity tip is seen in FIG. 8. Once again, similar reference numerals to those used in the second embodiment will be increased by 100. In this embodiment, the scoop wall 244 is linear in both the axial direction identical to that seen in FIG. 3 and in the radial direction as seen in FIG. 8. As in all other embodiments, the depth of the scoop tapers gently from its greatest point at the aperture edge 248 to its shallowest point at the terminal edge of the scoop 250. Once again, this embodiment preferably includes three fluid diverting scoops 240 and apertures (not shown); however, it is understood that as few as one scoop and more than three scoops could be incorporated into the wall 242 of the body portion 234. In addition, the three scoops 240 of this embodiment are preferably positioned at the same point along the length of the reduced velocity tip 224 and are equally spaced about the perimeter; however, it is understood that the scoops can be staggered along the length thereof or about the perimeter.

In another aspect, the invention is directed to the method of making an aortic cannula having the structure substantially as described above. The cannula body 14 and reduced velocity tip 24 according to the invention preferably have a one-piece construction manufactured by a dip-molding process in which a mandrel having the desired structure is dipped repeatedly into a bath of a suitable material, such as plastisol. First, the cannula body portion of the mandrel is dipped into a first bath of plastisol. After an initial layer is coated on the mandrel, then the spring is mounted on the mandrel. Next, the cannula body portion of the mandrel is once again dipped into the same plastisol bath. Next, the reduced velocity tip 24 portion of the mandrel is dipped into a bath of plastisol to create the desired structure. Preferably, the plastisol used for forming the tip 24 is more rigid than the plastisol used for the cannula body. The mandrel is dipped a sufficient amount so that there is direct, fused contact between the cannula body and the tip. After the body and tip have been molded on the mandrel, it is removed therefrom. In this molded condition, the distal flow aperture 38 and fluid discharge apertures 46 of the tip have not been formed. Therefore, a die is used to cut both the distal flow aperture 38 and the fluid discharge apertures 46. Preferably, the fluid discharge apertures are circular and are cut into the scoop 40 so that the linear axis of the center point of the circular aperture is parallel to the axis of the sidewall of the scoop 40. In the preferred embodiment, this axis extends radially outwardly at an angle of 15° from the axis of the lumen 36 of the body portion 34. After the formation of the fluid apertures, the cannula is then sent to conventional finishing operations such as smoothing sharp edges.

Those skilled in the art will recognize, or be able to ascertain, using no more than routine experimentation, many equivalents to the specific embodiments of the invention described herein. These and all other equivalents are intended to be encompassed by the following claims.

We claim:

1. An improved aortic cannula comprising a cannula body having a proximal end, a distal end, a lumen formed therein extending between the proximal and distal ends, and a tip provided on the distal end of the cannula body, the tip having a longitudinal axis, a tip body defined by a sidewall, a proximal end, a distal end, a lumen extending between the proximal and distal ends, and a plurality of fluid discharge apertures formed in the tip body, the improvement comprising:

an axial fluid discharge aperture provided at the distal end of the tip body, the axial fluid discharge aperture being substantially aligned with the axis of the lumen of the tip;

a lateral fluid discharge aperture provided in the sidewall of the tip, proximally of the axial fluid discharge, the lumen of the tip body having a prescribed cross-sectional area proximally of the lateral fluid discharge aperture, and the lumen of the tip body having a prescribed cross-sectional area distally from the lateral fluid discharge aperture, the cross-sectional area distally of the lateral fluid discharge aperture being substantially equal to or greater than the cross-sectional area proximally of the lateral fluid discharge aperture; and a diverting member formed in the sidewall of the tip immediately adjacent to the lateral fluid discharge, the diverting member extending radially inwardly into the lumen of the tip;

wherein, at least a portion of the fluid flowing through the tip exits the tip through the lateral fluid discharge aperture and the remainder of the fluid exits the tip through the axial fluid discharge aperture, the combination of the lateral and axial discharges having the effect of minimizing the aggregate velocity of the fluid exiting the tip.

2. An improved aortic cannula according to claim 1 and further comprising a plurality of lateral fluid discharge apertures provided in the sidewall of the tip, proximally of the axial fluid discharge aperture.

3. An improved aortic cannula according to claim 2 and further comprising a plurality of diverting members formed in the sidewall of the tip immediately adjacent to the lateral fluid discharge, each of the plurality of diverting members extending radially inwardly into the lumen of the tip.

4. An improved aortic cannula according to claim 3 and further comprising three lateral fluid discharge apertures and three diverting members.

5. An improved aortic cannula according to claim 4 wherein the three discharge apertures are equally spaced around the perimeter of the tip.

6. An improved aortic cannula according to claim 5 where the three discharge apertures are positioned at substantially the same point along the length of the tip.

7. An improved aortic cannula according to claim 1 wherein the diverting member is substantially linear in cross section parallel to the longitudinal axis of the lumen of the tip.

8. An improved aortic cannula according to claim 7 wherein the diverting member is substantially arcuate in cross section transverse to the longitudinal axis of the lumen of the tip.

9. An improved aortic cannula according to claim 7 wherein the diverting member is substantially linear in cross section transverse to the axis of the lumen of the tip.

10. An improved aortic cannula according to claim 1 wherein a first portion of the diverting member is substantially arcuate in cross section parallel to the axis of the lumen of the tip.

11. An improved aortic cannula according to claim 10 wherein the first portion of the diverting member is concave in relation to the sidewall of the tip.

12. An improved aortic cannula according to claim 10 wherein a second portion of the diverting member is substantially arcuate in cross section parallel to the axis of the lumen of the tip.

13. An improved aortic cannula according to claim 12 wherein the second portion of the diverting member is convex in relation to the sidewall of the tip.

14. An improved aortic cannula according to claim 13 wherein the first portion is positioned immediately adjacent the lateral fluid discharge aperture and the second portion is positioned distally from the first portion.

15. An improved aortic cannula comprising a cannula body having a proximal end, a distal end, a lumen formed therein extending between the proximal and distal ends, and a tip provided on the distal end of the cannula body, the tip having a longitudinal axis, a tip body defined by a sidewall, a proximal end, a distal end, and a lumen extending between the proximal and distal ends, the improvement comprising:

a distal fluid discharge aperture provided at the distal end of the tip body through which a portion of the fluid passing through the cannula exits the cannula; and a lateral fluid discharge aperture provided in the sidewall of the tip through which a portion of the fluid passing through the cannula exits the cannula, the lateral fluid discharge aperture being provided proximally of the distal fluid discharge aperture, wherein the lumen of the tip body has a prescribed cross-sectional area proximally of the lateral fluid discharge aperture and the lumen of the tip body has a prescribed cross-sectional area adjacent the distal fluid discharge aperture, the cross-sectional area distally of the lateral fluid discharge aperture being substantially equal to or greater than the cross-sectional area proximally of the lateral fluid discharge aperture, the combination of the removal of a portion of the fluid through the lateral fluid discharge in conjunction with the cross-sectional relationship of the distal and proximal portions of the tip serving to minimize the aggregate velocity of the fluid exiting the tip.

16. An improved aortic cannula according to claim 15 and further comprising a diverting member formed in the sidewall of the tip, the lateral fluid discharge being formed in the body of the diverting member so that the lateral fluid discharge aperture extends radially into the lumen of the tip, the diverting member being adapted to direct a portion of the fluid flowing through the cannula out of the cannula through the lateral fluid discharge aperture.

17. An improved aortic cannula according to claim 16 wherein a plurality of diverting members and a corresponding plurality of lateral fluid discharge apertures are provided in the sidewall of the tip.

18. An improved aortic cannula according to claim 17 wherein three diverting members and three corresponding lateral fluid discharge apertures are provided in the sidewall of the tip.

19. An improved aortic cannula according to claim 17 wherein the plurality of diverting members are equally spaced about the perimeter of the cannula tip.

20. An improved aortic cannula according to claim 17 wherein the plurality of diverting members are positioned at the substantially the same position along the longitudinal axis of the tip body.

21. An improved aortic cannula according to claim 16 wherein the diverting members are substantially linear in cross section parallel to the longitudinal axis of the tip.

22. An improved aortic cannula according to claim 21 wherein the diverting members are substantially linear in cross section transverse to the longitudinal axis of the tip.

23. An improved aortic cannula according to claim 21 wherein the diverting members are substantially arcuate in cross section transverse to the longitudinal axis of the tip.

24. An improved aortic cannula according to claim 16 wherein the diverting members are substantially arcuate in cross section parallel to the longitudinal axis of the tip.

25. An improved aortic cannula according to claim 24 wherein the diverting members are substantially arcuate in cross section transverse to the longitudinal axis of the tip.

26. A method of making an aortic cannula comprising the steps of:

providing a mandrel;

providing a liquid bath of plastisol;

dipping the mandrel into the bath of plastisol to create a molded cannula body, the body having a proximal end, a distal end and a lumen extending between the proximal and distal ends;

dipping the mandrel into the bath of plastisol to create a molded cannula tip, the tip having a proximal end, a distal end, a sidewall extending between the proximal and distal ends, a lumen extending between the proximal and distal ends and at least one fluid diverting member in the sidewall, the diverting member extending radially inwardly into the lumen of the molded cannula tip and the proximal end of the tip being fused to the distal end of the cannula body;

forming a plurality of fluid discharge apertures in the molded cannula tip, namely a distal fluid discharge aperture and at least one lateral fluid discharge aperture, the lateral fluid discharge aperture being formed in the at least one fluid diverting member, the lumen of the tip body having a prescribed cross-sectional area proximally of the lateral fluid discharge aperture, and the lumen of the tip body having a prescribed cross-sectional area distally from the lateral fluid discharge aperture, the cross-sectional area distally of the lateral fluid discharge aperture being substantially equal to or greater than the cross-sectional area proximally of the lateral fluid discharge aperture; and removing the molded cannula from the mandrel.

27. A method of making an aortic cannula according to claim 26 wherein the at least one lateral fluid discharge aperture is formed at an angle of fifteen degrees relative to the longitudinal axis of the cannula tip.

28. A method of making an aortic cannula according to claim 26 wherein three fluid diverting members and three lateral fluid discharge apertures are formed in the cannula tip.

* * * * *